(12) United States Patent
Beumer et al.

(10) Patent No.: US 11,078,178 B2
(45) Date of Patent: Aug. 3, 2021

(54) 6-CHROMANOL DERIVATIVES AND THEIR SYNTHESIS

(71) Applicant: DSM IP Assets B.V., Heerlen (NL)

(72) Inventors: Raphael Beumer, Kaiseraugst (CH); Werner Bonrath, Kaiseraugst (CH); Jan-Marc Delpho, Kaiseraugst (CH); Marcel Joray, Kaiseraugst (CH); Jonathan Alan Medlock, Kaiseraugst (CH); Thomas Netscher, Kaiseraugst (CH); Domenico Soriano, Kaiseraugst (CH); René Tobias Stemmler, Kaiseraugst (CH)

(73) Assignee: DSM IP ASSETS B.V., Heerlen (NL)

(*) Notice: Subject to any disclaimer, the term of this patent is extended or adjusted under 35 U.S.C. 154(b) by 0 days.

(21) Appl. No.: 16/642,546

(22) PCT Filed: Sep. 4, 2018

(86) PCT No.: PCT/EP2018/073745
§ 371 (c)(1),
(2) Date: Feb. 27, 2020

(87) PCT Pub. No.: WO2019/143251
PCT Pub. Date: Mar. 7, 2019

(65) Prior Publication Data
US 2020/0190051 A1 Jun. 18, 2020

(30) Foreign Application Priority Data
Sep. 4, 2017 (EP) .................................... 17189276

(51) Int. Cl.
| C07D 311/72 | (2006.01) |
| C07C 29/76 | (2006.01) |
| C07C 49/04 | (2006.01) |
| C07C 33/00 | (2006.01) |
| C07C 29/56 | (2006.01) |

(52) U.S. Cl.
CPC ............ *C07D 311/72* (2013.01); *C07C 29/56* (2013.01)

(58) Field of Classification Search
CPC ....... C07D 311/72; C07C 29/76; C07C 49/04; C07C 49/203; C07C 33/042; C07C 33/025
See application file for complete search history.

(56) References Cited

U.S. PATENT DOCUMENTS

| 4,347,388 A | 8/1982 | Gramlich et al. |
| 2003/0153485 A1 | 8/2003 | Markert et al. |

FOREIGN PATENT DOCUMENTS

| WO | 2005/026092 | 3/2005 |
| WO | 2014/056851 | 4/2014 |
| WO | 2015/117893 | 8/2015 |

OTHER PUBLICATIONS

International Search Report for PCT/EP2018/073745, dated Feb. 21, 2019, 7 pages.
Written Opinion of the ISA for PCT/EP2018/073745, dated Feb. 21, 2019, 8 pages.
Kamal-Eldin et al., "The chemistry and antioxidant properties of tocopherols and tocotrienols", Lipids, vol. 31, No. 7, Jul. 1996, pp. 671-701.
Cerecetto et al., "Antioxidants Derived from Vitamin E: An Overview", Mini Reviews in Medicinal Chemistry, vol. 7, No. 3, Mar. 2007, pp. 315-337.
Ofner et al., "Synthetisches Nerolidol Und Verwandte $C_{15}$-Alkohole", Helvetica Chimica Acta, vol. 17, No. 7, 1959, pp. 2577-2584.

*Primary Examiner* — Sikarl A Withersppon
(74) *Attorney, Agent, or Firm* — Nixon & Vanderhye P.C.

(57) ABSTRACT

The present invention relates to novel compounds which are particularly useful for the synthesis of novel chromanol derivatives. These compounds have interesting properties. Particularly, the novel chromanol derivatives have interesting antioxidant properties as well as flavours and fragrances.

18 Claims, 3 Drawing Sheets

6-CHROMANOL DERIVATIVES AND THEIR SYNTHESIS

Figure 1:
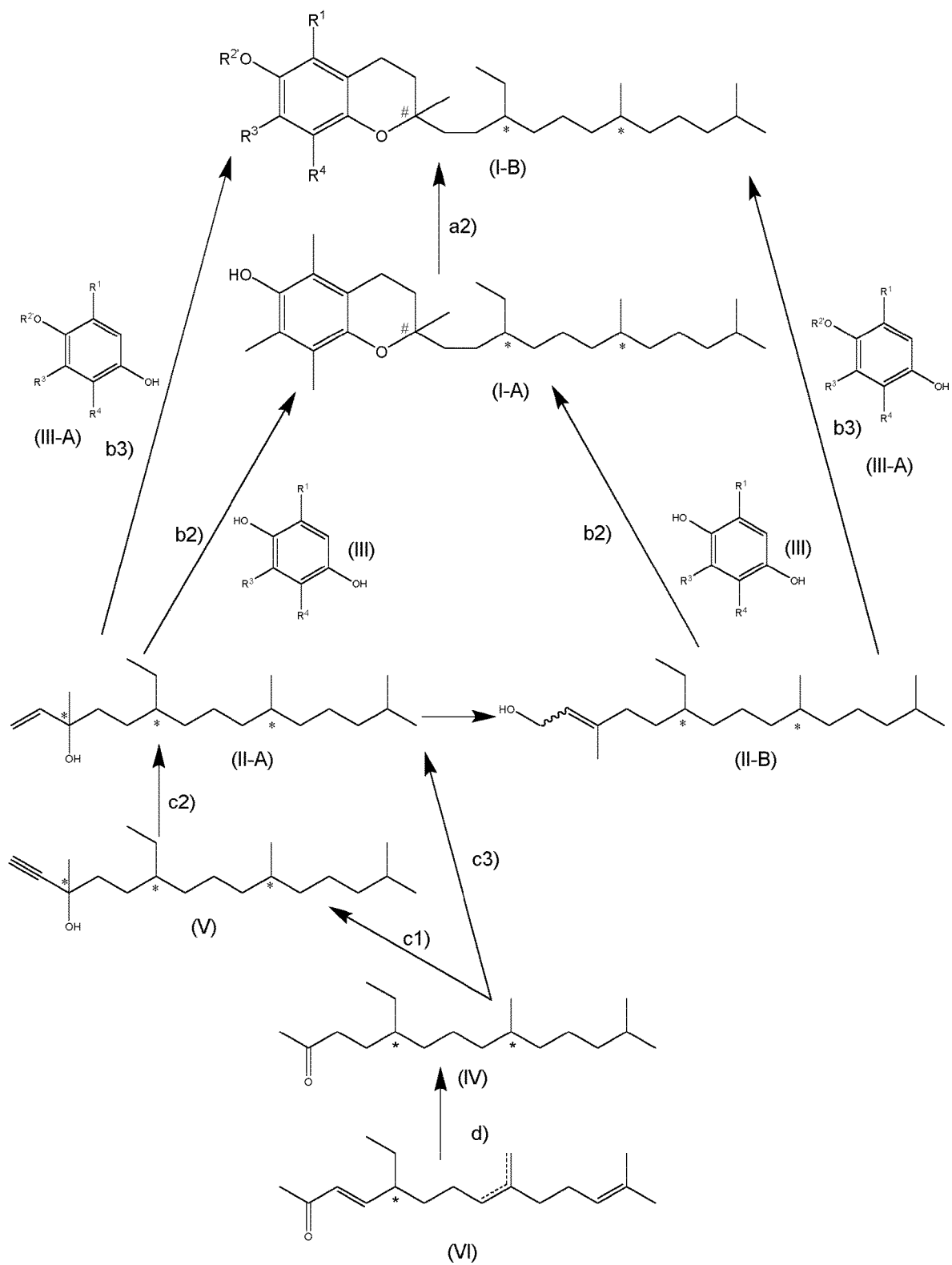

This application is the U.S. national phase of International Application No. PCT/EP2018/073745 filed 4 Sep. 2018, which designated the U.S. and claims priority to EP Patent Application No. 17189276.3 filed 4 Sep. 2017, the entire contents of each of which are hereby incorporated by reference.

TECHNICAL FIELD

The present invention relates to novel compounds which are particularly useful for the synthesis of novel chromanol derivatives.

BACKGROUND OF THE INVENTION

The field of isoprenoids and their derivatives is a field in chemistry, in which a lot of synthesis research has been carried out. One of the reasons is that they are precursors of vitamin E, particularly for alpha-tocopherol, which are very important compounds found in nature and important for the food and feed market. The isoprenoids beta-farnesene and beta-myrcene have been identified in this context as interesting starting compounds. Already more than 30 years ago, Rhône-Poulenc has researched this field intensively, e.g. U.S. Pat. Nos. 4,460,786, 4,621,165 and 5,874,636. CN 105859534 A and WO 2015/165959 A1 disclose beta-farnesene as potential starting material for the synthesis of farnesyl acetone.

Myrcene is a compound of natural origin and occurs in significant amounts in essential oil of several plants, including bay, *cannabis*, ylang-ylang, wild thyme, parsley, cardamom, and hops. In addition, it is manufactured from beta-pinene which is obtained from turpentine oil. Therefore, beta-myrcene is a readily available, sustainable, and interesting starting material for synthesis of more complex chemicals.

SUMMARY OF THE INVENTION

Surprisingly, we have found a whole series of compounds, not known up to now, with very interesting properties, which can be derived from myrcene. In a sequence of different reactions involving these novel compounds, a novel chromanol derivative has, finally, been found. This class of compounds has, amongst other properties, a particularly interesting antioxidant behaviour. Considering the close structural relationship to tocopherol, the novel compound is of highest interest for the research community and for the food and feed industry. Particularly important is its assessment of a potential impact in a living organism.

Furthermore, it has been found that the intermediates in this synthesis have interesting olfactory properties. Particularly, they have different odors and give raise to different olfactory impressions in comparison to those of the corresponding compounds which are already known.

This offers some very interesting new applications in the field of flavours and flagrances and particularly in the field of perfumes which is enabled by the compounds being accessible by the present invention. Odors in general, and complex olfactory impressions in particular, are very difficult or even impossible to predict. Therefore, any new odor giving alone or in combination an olfactory impression is of great value to the aroma, flavour and flagrance industry.

Further aspects of the invention are subject of further independent claims. Particularly preferred embodiments are subject of dependent claims.

DETAILED DESCRIPTION OF THE INVENTION

In a first aspect, the present invention relates to a compound of formula (I)

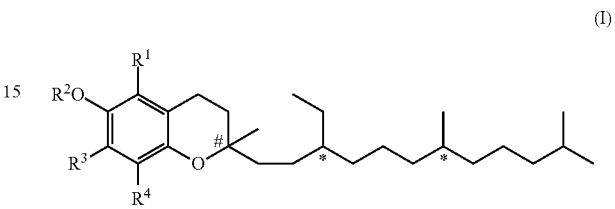

(I)

wherein $R^1$, $R^3$ and $R^4$ represent independently from each other hydrogen or methyl groups;
$R^2$ represents hydrogen or $R^{2'}$ which is a phenol protecting group; and wherein each * marks a chiral/stereogenic centre, and # marks a chiral/stereogenic centre.

For sake of clarity in the following some terms as been used in the present document are defined as followed:

In the present document, a "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH(CH$_3$)—CH$_2$—CH$_3$ is considered as a $C_4$-alkyl group.

A "$C_{x-y}$-alkylene" group is an alkylene group comprising x to y carbon atoms, i.e., for example, a $C_{1-3}$-alkylene group is an alkylene group comprising 1 to 3 carbon atoms. The alkylene group can be linear or branched. For example, —CH$_2$—CH$_2$—CH$_2$— and —CH(CH$_3$)—CH$_2$— and —C(CH$_2$—CH$_3$)— and —C(CH$_3$)$_2$— are all considered as a $C_3$-alkylene group.

In case identical labels for symbols or groups are present in several formulae, in the present document, the definition of said group or symbol made in the context of one specific formula applies also to other formulae which comprises said same label.

The expression "process of preparation" is a synonym for "method of preparation" and can be used interchangeable to each other.

The configuration of an asymmetrically substituted carbon centre is indicated by the label R or S according to the rules defined by R. S. Cahn, C. K. Ingold and V. Prelog. This R/S-concept and rules for the determination of the absolute configuration in stereochemistry is known to the person skilled in the art.

In the present document, any dotted single line in formulae represents the bond by which a substituent is bound to the rest of a molecule.

Any wavy line in any formula of this document represents a carbon-carbon bond which is linked to an adjacent carbon-carbon double bond so as to have said carbon-carbon double bond either in the Z- or in the E-configuration. In other words, a formula having a wavy line represents a formula covering the E as well as the Z isomer.

* and # in any formula of this document mark an asymmetrically substituted carbon atom, which is a chiral/stereogenic centre.

In formula (I), $R^2$ represents either hydrogen or a phenol protecting group. Hence, formula (I) embraces two embodiments. These two embodiments are of formula (I-A) or (I-B), as discussed in the following.

In one embodiment of the invention $R^2$ represents hydrogen. In this case the compound of formula (I) is a compound of formula (I-A).

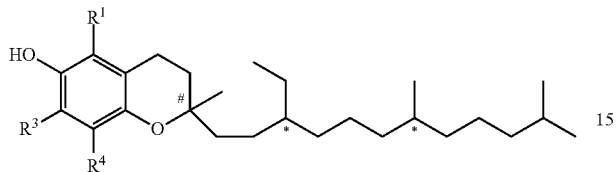
(I-A)

In another embodiment of the invention, $R^2$ is $R^{2'}$ which represents a phenol protecting group. Therefore, this embodiment of formula (I) has the formula (I-B)

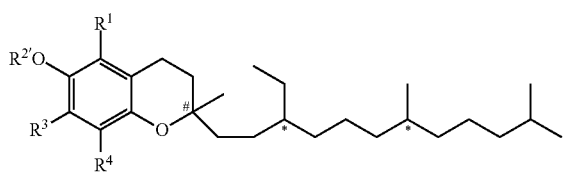
(I-B)

in which $R^{2'}$ represents a phenol protecting group.

A phenol protecting group is a group which protects the phenolic group (OH in formula (I-A)) and the protecting group can be easily removed, i.e. by state-of-the-art methods, resulting to the respective compound with the free phenolic group again.

The phenol protecting group is introduced by a chemical reaction of the compound of formula (I-A) with a protecting agent.

The protecting agents leading to the corresponding phenol protecting groups are known to the person skilled in the art, as well as the chemical process and conditions for this reaction. If, for example, the phenol protecting group forms with the rest of the molecule an ester, the suitable protecting agent is for example an acid, an anhydride, or an acyl halide.

The phenol protecting group $R^{2'}$ is particularly selected from the groups consisting of

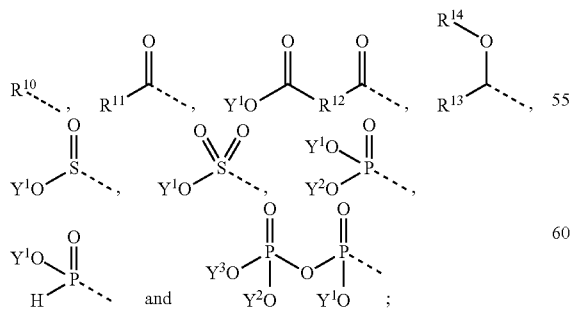

wherein $R^{10}$ and $R^{11}$ represent independently from each other a $C_{1-15}$-alkyl or a fluorinated $C_{1-15}$-alkyl or a $C_{1-15}$-cycloalkyl or a $C_{7-15}$-aralkyl group;

$R^{12}$ represents a $C_{1-15}$-alkylene or a $C_{6-15}$-alkylene group; and wherein either $R^{13}$ represents a $C_{1-15}$-alkyl group or an alkyleneoxyalkyl group or a polyoxyalkylene group;

$R^{14}$ represents hydrogen or a $C_{1-15}$-alkyl group;

or $R^{13}$ and $R^{14}$ represent together a $C_{3-7}$-alkylene group forming a 5 to 7 membered ring;

and wherein $Y^1$, $Y^2$ and $Y^3$ represent independently from each other hydrogen or a group of the formula

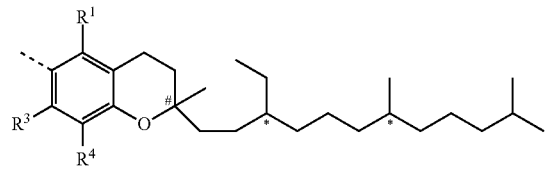

and wherein the single dotted line represents the bond by which said substituent is bound to the rest of a molecule.

If $R^{2'}$ is equal to $R^{10}$, the compound of formula (I) is an ether, which can be formed by the reaction of the respective protecting agent with the phenolic group (OH) of compound of formula (I-A). In this case, the protecting agent may be for example an alkylation agent such as the respective $C_{1-15}$-alkyl or fluorinated $C_{1-15}$-alkyl or $C_{1-15}$-cycloalkyl or $C_{7-15}$-aralkyl halide, particularly iodide.

In one of the preferred embodiments $R^{10}$ is a methyl group.

In another preferred embodiment $R^{10}$ is a $C_{7-15}$-aralkyl group, preferably a benzyl group or a substituted benzyl group, particularly preferred a benzyl group. If $R^{2'}$ is represented by

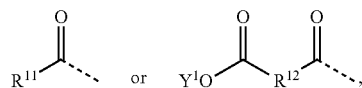

the compound of formula (I) is an ester of a carboxylic acid or dicarboxylic acid, which can be formed by the reaction of the respective protecting agent with the phenolic group (OH) of compound of formula (I-A). In this case, the protecting agent may be for example an anhydride or halide of the respective carboxylic acid (1) or dicarboxylic acid (2).

(1)

(2)

If the compound of formula (I) is an ester of a carboxylic acid or dicarboxylic acid, it is preferred that $R^{2'}$ is an $C_{1-7}$-acyl, preferably acetyl, trifluoroacetyl, propionyl or benzoyl group, or a substituted benzoyl group.

Esters can be easily deprotected under the influence of an acid or a base.

If R[2'] is

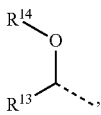

the compound of formula (I) is an acetal, which can be formed by the reaction of the respective protecting agent with the phenolic group (OH) of compound of formula (I-A). In this case, the protecting agent may be for example, a respective aldehyde, alkyl halide, e.g. MeO(CH$_2$)$_2$OCH$_2$Cl, or an enol ether, e.g. 3,4-dihydro-2H-pyran.

In this case, the substituent R[2'] is preferably

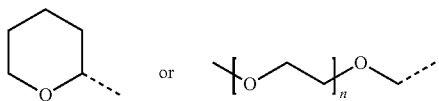

with n=0 or 1.

In some instances, acetals are also called "ethers", particularly in the cases mentioned above: methoxymethyl ether (MOM-ether), β-methoxyethoxy-methyl ether (MEM-ether) or tetrahydropyranyl ether (THP-ether).

Acetals can be easily deprotected under the influence of acids.

In another preferred embodiment, the compound of formula (I) is an ester of phosphoric acid, pyrophosphoric acid, phosphorous acid, sulphuric acid or sulphurous acid.

Depending on the reaction conditions, the esterification is either complete or partial, leaving some residual acid groups of the respective acid non-esterified (i.e. Y$^1$ and/or Y$^2$ and/or Y$^3$=H).

It is most preferred that the protecting group R[2'] is a benzoyl group or a C$_{1-4}$-acyl group, particularly acetyl or trifluoroacetyl group, more particularly acetyl group. The molecules in which R[2'] represents an acyl group, particularly an acetyl group, can be easily prepared from the corresponding unprotected molecule by esterification, and the unprotected phenolic compound can be obtained from the corresponding ester by ester hydrolysis.

R$^1$, R$^3$ and R$^4$ represent independently from each other hydrogen or methyl groups.

Preferred in all formulae of the present invention, are the following combinations of R$^1$, R$^3$ and R$^4$:

R$^1$=R$^3$=R$^4$=CH$_3$
or
R$^1$=R$^4$=CH$_3$, R$^3$=H
or
R$^1$=H, R$^3$=R$^4$=CH$_3$
or
R$^1$=R$^3$=H, R$^4$=CH$_3$.

Most preferred is the substitution pattern R$^1$=R$^3$=R$^4$=CH$_3$.

As mentioned above, the compound of formula (I) in which the residue R$^2$ stands for R[2'], being a protecting group, can be obtained from compound of formula (I-A). Therefore, in a further aspect, the present invention relates to a process of manufacturing a compound of formula (I-B) comprising the steps a1) providing a compound of formula (I-A)

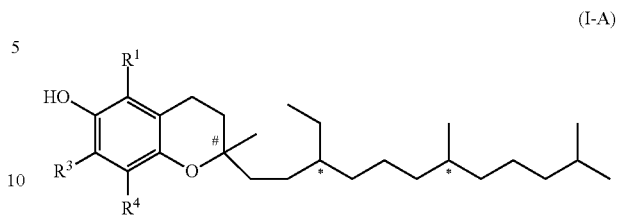

a2) reacting the compound of formula (I-A) with a protecting agent to yield the compound of formula (I-B)

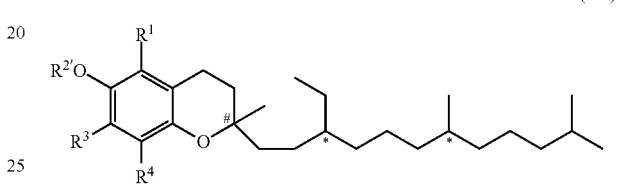

Compound of formula (I-A) can be prepared in various ways. In a particularly suitable manner it is synthesized from a compound of formula (II-A) or (II-B) with a compound of formula (III).

Therefore, in a further aspect, the present invention relates to a process of manufacturing a compound of formula (I-A) comprising the steps b1) providing a compound of formula (II-A) or (II-B);

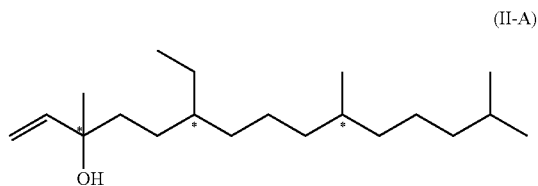

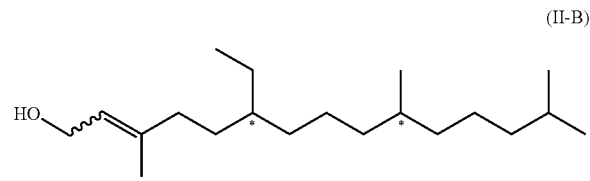 [SMILES: CCC(CCCC(C)CCCC(C)C)CCC(C)=CCO]

b2) condensing the compound of formula (II-A) or (II-B) with a compound of formula (III) to yield the compound of formula (I-A)

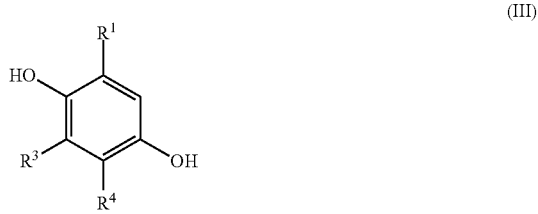

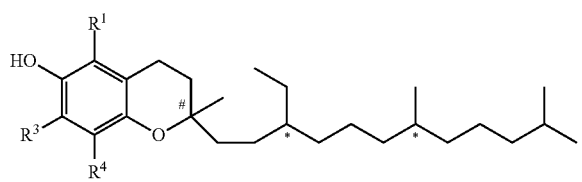
(I-A)

It has been found that the condensation reaction of step b2) can be performed in analogy to the condensation of methyl-, dimethyl- respectively trimethylhydroquinone and the corresponding alcohol isophytol or phytol as described for example in Ullmann's Encyclopedia of Industrial Chemistry, Release 2010, 7th Edition, "Vitamins", page 44-46.

For this condensation reaction (step b2)) a series of catalysts may be used such as ZnCl$_2$/mineral acid, BF$_3$/AlCl$_3$, Fe/HCl, trifluoroacetic acid or boric acid/carboxylic acid as well as indium(III) or scandium(III) salts as disclosed in WO 2005/121115 A1. Furthermore, suitable catalysts are heteropoly acids, particularly 12-tungstophosphoric acid or 12-tungstosilicic acid such as disclosed in EP 0 970 953 A1.

In the condensation step b2) a novel compound of formula (I-C) is obtained as intermediate

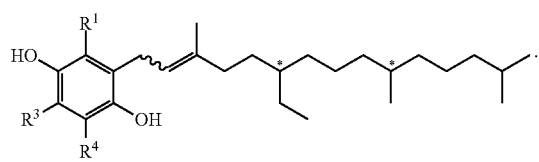
(I-C)

Compound of formula (I-C) represents, thus, a further aspect of the present invention.

A further method of preparing a compound of formula (I-B) represents another aspect of the present invention. This method comprises the steps b1) providing a compound of formula (II-A) or (II-B);

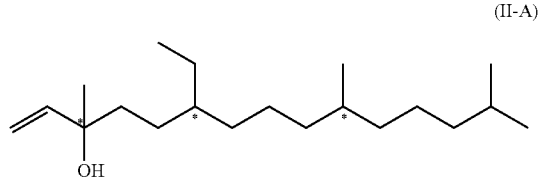 [SMILES: C=CC(C)(O)CCC(CC)CCCC(C)CCCC(C)C]
(II-A)

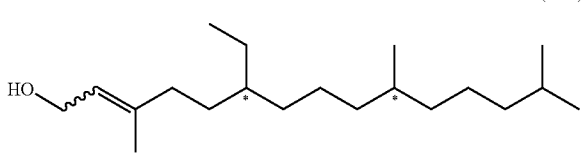
(II-B)

b3) condensing the compound of formula (II-A) or (II-B) with a compound of formula (III-A) to yield the compound of formula (I-B)

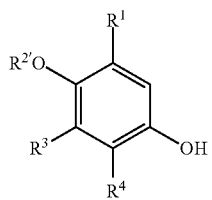
(III-A)

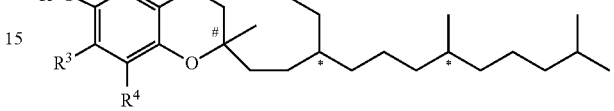
(I-B)

In the condensation step b3) a novel compound of formula (I-D) is obtained as intermediate

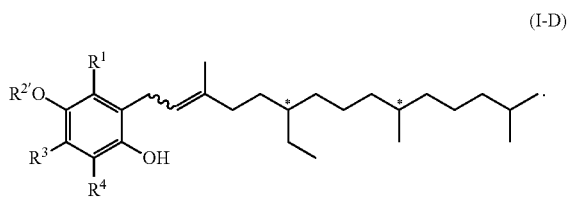
(I-D)

Compound of formula (I-D) represents, thus, a further aspect of the present invention.

The reactions mentioned above are not stereospecific and, hence, a mixture of isomers of formula (I-A) or (I-B) of R- and S-configuration at the chiral/stereogenic centre marked by # at C-2 is formed. Typically, a diastereomeric mixture of about 50% 2S- and 50% 2R-isomers are formed at C-2 of formula (I-A).

The different stereoisomers can be principally separated and isolated by techniques based on chromatography, particularly using chiral stationary phases, particularly as those described in WO 2016/188945 A1 or WO 2012/152779 A1, the entire content of which is hereby incorporated by reference.

Therefore, it is possible to obtain a specific stereoisomer of formula (I) or (I-A) in which the chiral/stereogenic centres marked by * and/or #, particularly the chiral/stereogenic centre marked by #, possess the desired configuration.

Hence, this methodology facilitates/permits access to compounds of formula (I) or (I-A) in a specific configuration, particularly (2R,3'R,7'R), as shown in the formulae below:

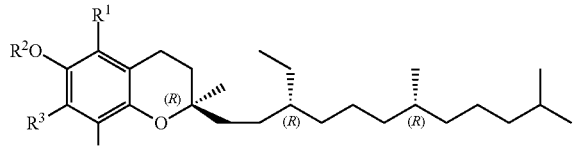

The compounds of formula (II-A) and (II-B) mentioned above are novel and represent two further aspects of the present invention.

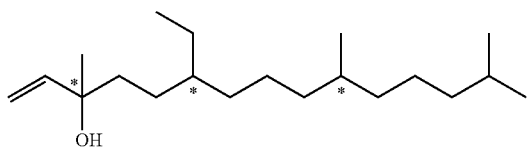

(II-A)

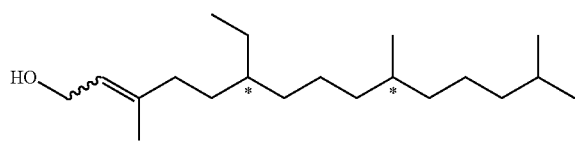

(II-B)

Besides being intermediates in the synthesis of compound of formula (I) resp. (I-A), they can also be used in the field of flavours and flagrances and particularly in the field of perfumes due to their odor.

We have found that the above compound of formula (II-B) can be obtained from compound of formula (II-A) by isomerization. Therefore, in a further aspect, the present invention relates to a process of manufacturing the compound of formula (II-B)

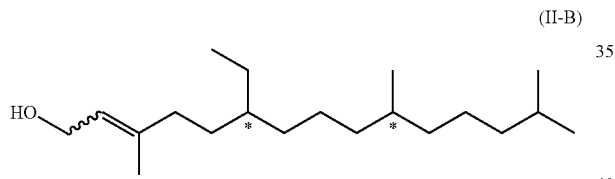

(II-B)

by isomerization of a compound of formula (II-A)

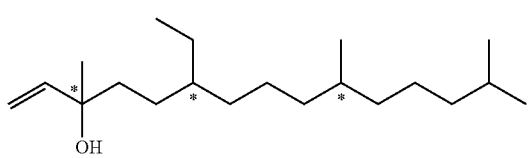

(II-A)

wherein the wavy line represents a carbon-carbon bond which when linked to the carbon-carbon double bond is either in the Z- or in the E-configuration.

The methods for isomerization can be those as known to the person skilled in the art for the isomerization of isophytol to phytol by acid-catalyzed rearrangement as described for example in Ullmann's Encyclopedia of Industrial Chemistry, Release 2010, 7th Edition, "Vitamins", page 44-46.

We have found that the above compound of formula (II-A) can be obtained from compound of formula (IV). Therefore, in a further aspect, the present invention relates to a process of manufacturing the compound of formula (II-A)

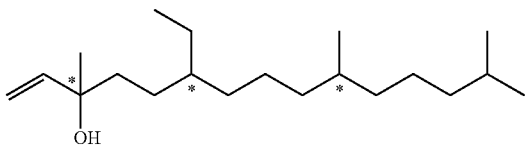

(II-A)

comprising the step b) providing a compound of formula (IV);

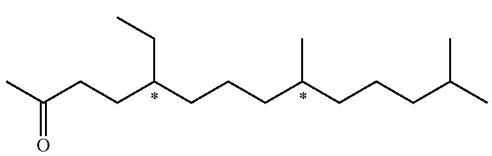

(IV)

followed by the steps either c1) ethynylation of the compound of formula (IV) using ethyne in the presence of a basic substance to yield a compound of formula (V)

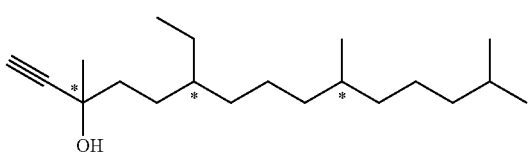

(V)

c2) hydrogenation of the compound of formula (V) with molecular hydrogen in the presence of a Lindlar catalyst to yield the compound of formula (II-A);

or c3) vinylation of the compound of formula (IV) by addition of a vinyl Grignard reagent to yield the compound of formula (II-A).

Details for the reaction type and conditions which can be used for the variant using steps c1) is disclosed in EP 1 532 092 B1, particularly in example 2, or WO 2003/029175 A1 (using a basic anion exchange resin), the entire content of which is hereby incorporated by reference. The hydrogenation with molecular hydrogen in the presence of a Lindlar catalyst can be used for step c2). For example, method and conditions disclosed by A. Ofner et al., Helv. Chim. Acta 1959, 42, 2577-2584 can be used for the combination of steps c1) and c2), the entire content of which is hereby incorporated by reference.

U.S. Pat. No. 4,028,385, for example, discloses details for the reaction type and conditions of the variant using step c3) as well as also for steps c1) and c2), the entire content of which is hereby incorporated by reference.

The compound of formula (V) mentioned above is novel and represents a further aspect of the present invention.

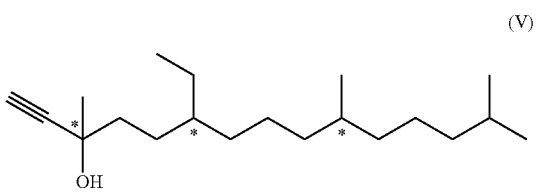 [SMILES: C#CC(C)(O)CCC(CC)CCCC(C)CCCC(C)C]

As discussed above, the compound of formula (V) can be manufactured by a reaction c1), i.e. by ethynylation of the compound of formula (IV) using ethyne in the presence of a basic substance.

The compound of formula (IV) mentioned above is also novel and represents a further aspect of the present invention.

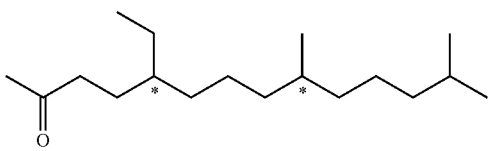

We have found that this compound of formula (IV) can be obtained from a compound of formula (VI). Therefore, in a further aspect, the invention relates to a process of manufacturing the compound of formula (IV)

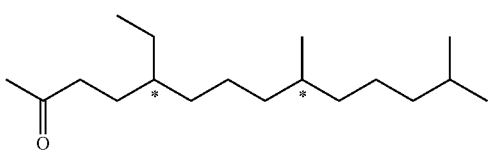

comprising the step d) hydrogenation of a compound of formula (VI) to yield the compound of formula (IV)

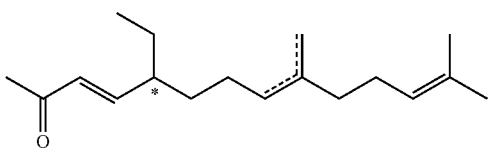

wherein the dotted line indicates a carbon-carbon double bond which is located at one of the two indicated positions.

In other words, the formula of this compound (VI), shown above, is a schematic representation of the following two formulae (VI-a) and (VI-b)

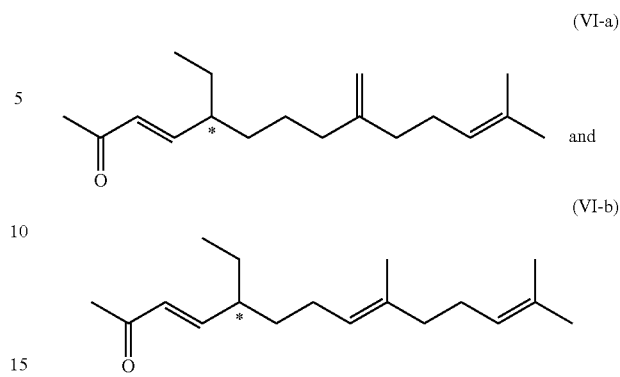

In fact, as not only pure molecules of either the formula (VI-a) or (VI-b), but also a mixture of formulae (VI-a) and (VI-b), can be used a starting material for the hydrogenation in step d). They all yield the same product, i.e. compound of formula (IV).

It is preferred that for this reaction a mixture of formulae (VI-a) and (VI-b) are used as compound of formula (VI) in step d) above.

The compound of formula (VI) mentioned above is also novel and represents a further aspect of the present invention.

The hydrogenation of the compound of formula (VI), respectively (VI-a) and/or (VI-b), to the compound of formula (IV) can be performed in step d) according to a method generally known by the person skilled in the art. Typically the hydrogenation involves a reaction with molecular hydrogen in the presence of a noble metal catalyst. Preferably, the hydrogenation is performed by means of molecular hydrogen in the presence of a palladium on a mineral carrier. Particularly preferred is the noble metal catalyst selected from the group consisting of palladium on carbon, palladium on silica ($SiO_2$), palladium on $TiO_2$ and palladium on aluminum oxide ($Al_2O_3$).

The hydrogenation in step d) is preferably made under pressure, particularly under a pressure of between 1 and 20 bar, more preferably between 1 and 6 bar.

It has been shown that compound of formula (VI), respectively (VI-a) or (VI-b), can be obtained from a compound of formula (VII) by a reaction e).

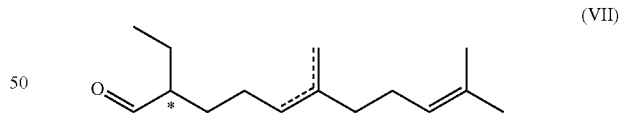

The dotted line in formula (VII) indicates a carbon-carbon double bond which is located at one of the two indicated positions.

In other words, the formula of this compound (VII), shown above, is a schematic representation of the following two formulae (VII-a) and (VII-b)

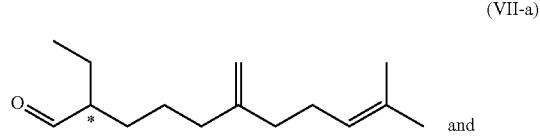

-continued

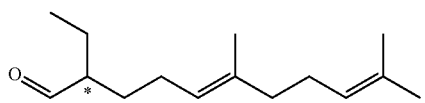
(VII-b)

Said reaction e) particularly is a Wittig reaction which comprises the reaction of compound of formula (VII), respectively (VIII-a) or (VII-b), with 1-(tri-phenylphosphoranylidene)-2-propanone.

The compound of formula (VII) mentioned above is also novel and represents a further aspect of the present invention.

It has been shown that the compound of formula (VII), respectively (VII-a) or (VII-b) can be obtained from a compound of formula (VIII), respectively (VIII-a) or (VIII-b) by a reaction f).

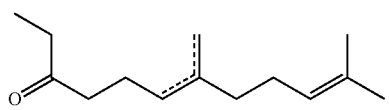
(VIII)

The dotted line in formula (VIII) indicates a carbon-carbon double bond which is located at one of the two indicated positions.

In other words, the formula of this compound (VIII), shown above, is a schematic representation of the following two formulae (VIII-a) and (VIII-b)

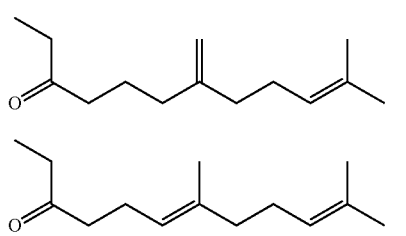
(VIII-a)

and (VIII-b)

Reaction f) consists of a Wittig reaction of ketones of formula (VIII) with an (alkoxymethyl)triarylphosphonium salt in the presence of a base, followed by hydrolysis of the formed enol ether under acidic conditions to the corresponding aldehyde.

It has been shown that the compound of formula (VIII), respectively (VIII-a) or (VIII-b), can be obtained from a compound of formula (IX), respectively (IX-a) or (IX-b), by a reaction g).

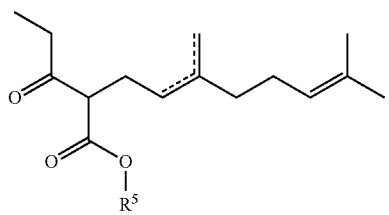
(IX)

The dotted line in formula (IX) indicates a carbon-carbon double bond which is located at one of the two indicated positions.

In other words, the formula of this compound (IX), shown above, is a schematic representation of the following two formulae (IX-a) and (IX-b)

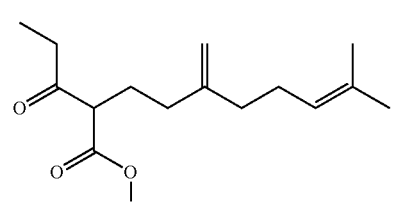
(IX-a)

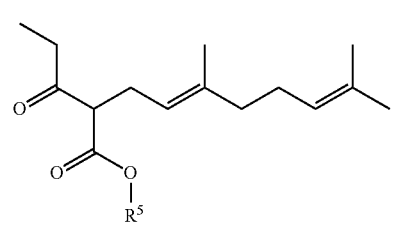
(IX-b)

Reaction g) involves a decarboxylation in the presence of water. Details for this reaction for analogous compounds can be found in U.S. Pat. No. 5,874,636.

It has been shown that the compound of formula (IX), respectively (IX-a) or (IX-b), can be obtained from myrcene (formula (X)) and a compound of formula (XI)

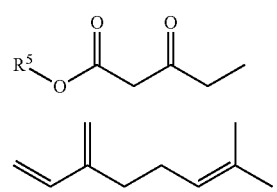
(XI)

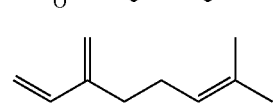
(X)

in the presence of a noble metal catalyst, particularly of a rhodium (I) catalyst, most preferred a rhodium (I) complex having a suitable diene or ethyne as ligand, particularly in the presence of a water-soluble phosphine. Suitable dienes are particularly 1,5-cyclooctadiene or norbornadiene. The preferred ligand is 1,5-cyclooctadiene.

This reaction is advantageously performed according to the methods as described in the Rhône-Poulenc patents U.S. Pat. Nos. 4,460,786 and 4,621,165, the entire content of which is hereby incorporated by reference.

In formulae (IX), (IX-a), (IX-b) and (XI), the residue $R^5$ stands for a $C_{1-10}$-alkyl group, preferably for a $C_{1-5}$-alkyl group, more preferably for a methyl group.

Figure 2:
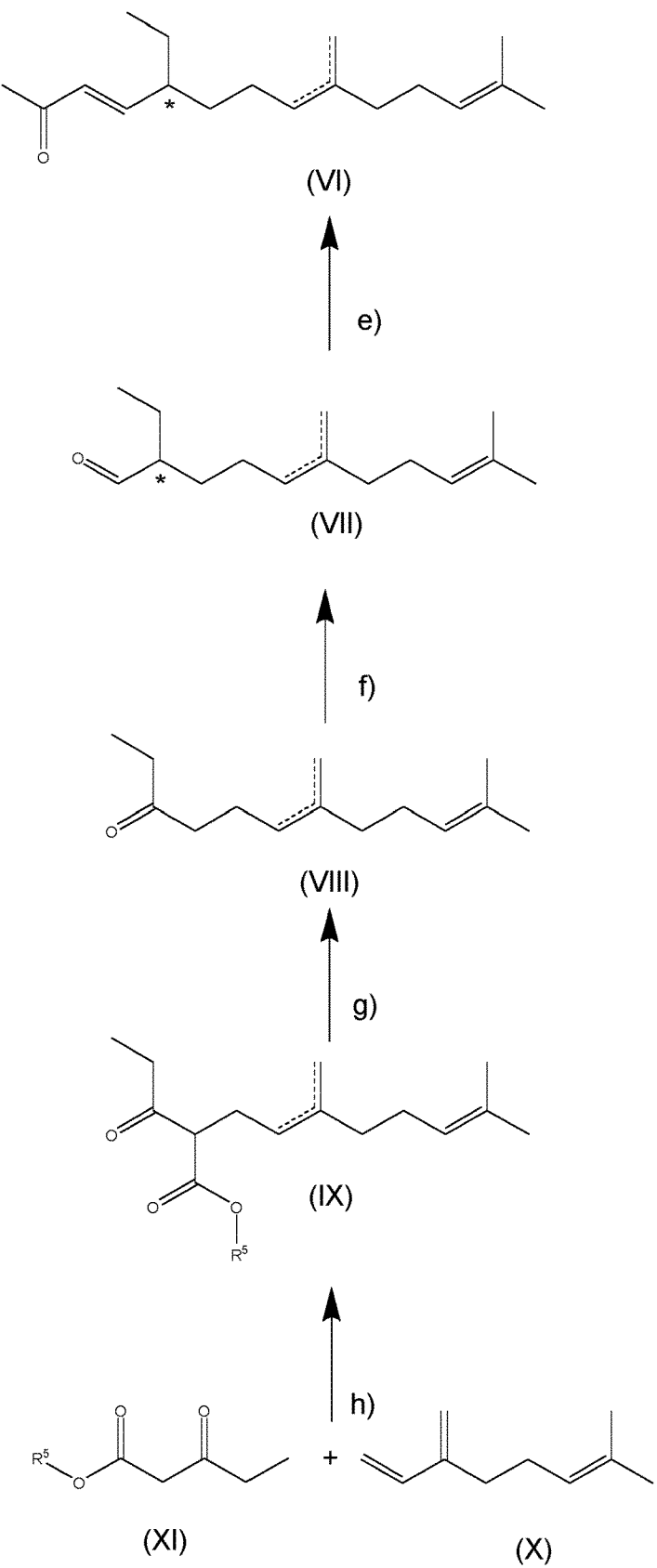

In FIGS. 1 and 2, a scheme of the disclosed synthetic pathway for compound of formula (I) is shown. This synthetic pathway starts from the commercially available starting materials myrcene (formula (X)) and alkyl 3-oxovalerate (XI), and uses different intermediates particularly of formula (VII), (VI), (IV), (V), (II-A), (II-B) and (I-A). Details for these substances and their process of manufacturing in the specific reaction steps are disclosed in the description above.

It has been observed that the substances described above, particularly the compounds of formulae (IV), (V), (VI), (VII), (VIII), (IX), (II-A) or (II-B), particularly of formulae (IV), (VI), (VII), (V), (II-A) or (II-B) or particularly of formulae (IV), (VI), (VII), (VIII) or (IX), have a variety of interesting properties and can be used for a multitude of purposes. Particularly, they are very interesting for being used in the field of flavours and flagrances and particularly in the field of perfumes and as starting material for molecules in the field of pharma, food, and feed additives. They have very interesting odors, particularly wood, fruit to even floral notes which makes it very appealing to use these substances in the field of flavours and flagrances and perfumes. Particularly interesting are those substances to be used with other olfactory active substances to create new olfactory impressions.

The compounds mentioned above may be used in a broad range of fragrance applications, e.g. in any field of fine and functional perfumery, such as perfumes, household products, laundry products, body care products and cosmetics. The compound can be employed in widely varying amounts, depending upon the specific application and on the nature and quantity of other odorant ingredients.

The compounds may be employed into the fragrance application simply by directly mixing the fragrance composition with the fragrance application, or they may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release said new compounds upon application of an external stimulus such as light, enzyme, or the like, and then mixed with the application. As used herein, "fragrance application" means any product, such as fine perfumery, e.g. perfume and eau de toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odorant. This list of products is given by way of illustration and is not to be regarded as being in any way limiting.

Furthermore, it has been surprisingly found that compound of formula (I) has particularly interesting antioxidant behaviour. Considering the close structural relationship to tocopherol, the novel compound is of highest interest for the research community and for the food and feed industry. Particularly important is its assessment of a potential impact in a living organism.

Particularly interesting is any combination of compound of formula (I) with other antioxidants. A suitable other antioxidant is particularly an antioxidant selected from the group consisting of butylated hydroxytoluene (BHT), butylated hydroxyanisole (BHA), tert-butylhydroquinone (TBHQ), propyl gallate, vitamin A, vitamin C and vitamin E.

Particularly interesting are compositions comprising a compound of formula (I) and a compound of formula (XI)

(I)

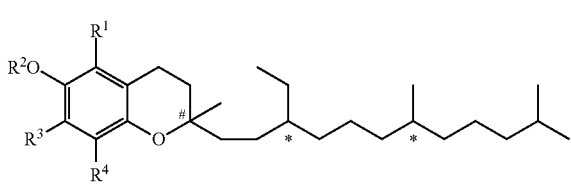

(XI)

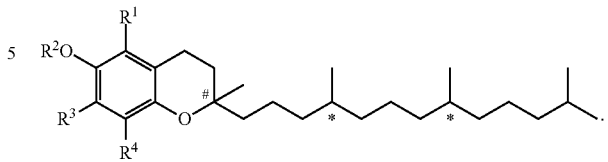

EXAMPLES

The present invention is further illustrated by the following experiments.

Example 1

Example of Compound of Formula (IX): Synthesis of methyl 2-geranyl-3-oxovalerate Reaction Step: h)

A 200 mL four-necked sulfonation flask, equipped with magnetic stir bar, condenser, thermometer and argon adapter, was inertized with argon and then charged with $Na_2CO_3$ (42 mg, 0.40 mmol, 99.8%, 0.4 mol %), chloro(1,5-cyclo-octadiene)rhodium(I) dimer (60 mg, 0.12 mmol, 0.24 mol % [Rh]), sodium 3,3',3''-phosphanetriyltribenzenesulfonate (3.56 g, 5.95 mmol, 95%, 6 mol %) and dissolved in water (26 mL) and MeOH (6 mL). Methyl 3-oxovalerate (15 mL, 15.7 g, 119 mmol, 1.2 equivalents) and myrcene (19.0 mL, 15 g, 99 mmol, 90%, 1.0 equivalent) were added and the biphasic mixture was heated to 100° C. (oil bath) for 23 h. The mixture was allowed to cool to 23° C. and the phases were separated. The organic phase was diluted with hexane (50 mL), then washed with brine (2×50 mL), dried over $MgSO_4$, filtered and concentrated in vacuo to give 24.0 g of crude, colorless product. Subsequently, the product was purified by vacuum distillation at 145° C. (oil bath)/0.35 mbar, furnishing a two isomer-mixture of methyl 2-geranyl-3-oxovalerate (methyl (E)-5,9-dimethyl-2-propionyldeca-4,8-dienoate and methyl 9-methyl-5-methylene-2-propionyldec-8-enoate) as colorless liquid (18.63 g, 95.7% purity by qNMR, 68% yield). The two isomers have been characterized by MS and NMR.

Characterization of methyl 2-geranyl-3-oxovalerate

GC-MS method. GC: column HP-5MS, 30 m×0.25 mm, 0.25 μm; temperature ramp: 70° C., +10° C./min to 315° C., hold 15 min. Total run time 39.5 min. MS: quadrupole mass spectrometer, EI.

GC-MS: 51.5 area % (methyl 9-methyl-5-methylene-2-propionyldec-8-enoate), 41.7 area % (methyl (E)-5,9-dimethyl-2-propionyldeca-4,8-dienoate).

m/z (methyl 9-methyl-5-methylene-2-propionyldec-8-enoate, %) 266 (2, M+), 248 [5, (M-$H_2O$)+], 205 (6), 136 (22), 121 (21), 109 (26), 93 (78), 69 (100), 57 (43), 41 (45), 29 (20).

m/z (methyl (E)-5,9-dimethyl-2-propionyldeca-4,8-dienoate, %) 266.1 (2, M+), 248 [1, (M-$H_2O$)+], 197 (10), 137 (29), 136 (29), 121 (19), 109 (58), 93 (19), 81 (20), 69 (71), 57 (100), 41 (44), 29 (22).

$^1$H NMR (mixture of isomers, 300 MHz, CHLOROFORM-d) δ 1.05 (t, J=7.3 Hz, 1.4H), 1.06 (t, J=7.3 Hz, 1.6H), 1.56-1.63 (m, 4.5H), 1.64-1.70 (m, 3H), 1.92-2.15 (m, 6.5H), 2.40-2.68 (m, 3H), 3.43-3.52 (m, 1H), 3.70 (s, 1.3H), 3.72 (s, 1.7H), 4.72 (br s, 0.56H), 4.77 (d, J=1.3 Hz, 0.57H), 4.97-5.14 (m, 1.5H) ppm.

$^{13}$C NMR (mixture of isomers, 75 MHz, CHLOROFORM-d) δ 7.53, 7.59, 16.0, 17.63, 17.64, 25.6, 26.19, 26.28, 26.5, 27.1, 33.7, 35.4, 35.6, 39.6, 52.22, 52.27, 57.8, 58.5, 110.2, 119.7, 123.86, 123.93, 131.5, 131.7, 138.4, 147.9, 170.08, 170.28, 205.64, 205.66 ppm.

Example 2: Compound of Formula (VIII): Synthesis of 11-methyl-7-methylenedodec-10-en-3-one and (E)-7,11-dimethyldodeca-6,10-dien-3-one Reaction step: g)

A 100 mL four-necked flask, equipped with magnetic stirrer, condenser, Dean-Stark trap, thermometer, argon adapter, syringe pump and oil bath, was charged with methyl 2-geranyl-3-oxovalerate (example 1) (mixture of two olefin isomers, 17.6 g, 63.3 mmol, 95.7% by qNMR). The flask was heated to 190° C. (oil bath), after which water (2.0 mL, 1.75 equivalents) was added slowly below surface via syringe pump over 8 h. The reaction was continued for another 13 h at 190° C. (oil bath), after which the crude product was cooled to room temperature and diluted with hexane (50 mL). The solution was washed with water (3×50 mL), and the combined aqueous phases were backextracted with hexane (30 mL). The combined organic phases were dried over MgSO$_4$, filtered and concentrated in vacuo (40° C., 120 to 1 mbar) to a colorless residue (12.9 g). The crude product was purified by distillation, furnishing a mixture of 11-methyl-7-methylenedodec-10-en-3-one and (E)-7,11-dimethyldodeca-6,10-dien-3-one (10.2 g, 48.7 mmol, 99.3% by qNMR, ratio ~54:46, 77% yield).

Characterization of Compound of Formula (VIII)

GC-MS: 53.6 area % (11-methyl-7-methylenedodec-10-en-3-one), 44.2 area % ((E)-7,11-dimethyldodeca-6,10-dien-3-one);

m/z (11-methyl-7-methylenedodec-10-en-3-one, %) 208 (2, M$^+$), 190 [3, (M-H$_2$O)$^+$], 175 (2), 165 (9), 147 (9), 136 (16), 121 (15), 109 (30), 93 (42), 85 (15), 79 (9), 69 (100), 57 (38), 41 (49), 29 (16).

m/z ((E)-7,11-dimethyldodeca-6,10-dien-3-one, %) 208 (2, M$^+$), 190 [1, (M-H$_2$O)$^+$], 175 (0.5), 165 (15), 147 (2), 136 (14), 121 (11), 109 (7), 93 (10), 81 (5), 69 (40), 57 (100), 41 (27), 29 (14).

$^1$H NMR (mixture of double bond isomers, 300 MHz, CHLOROFORM-d) δ 1.06 (t, J=7.3 Hz, 3H), 1.60 (br s, 1.5H), 1.61 (br s, 3H), 1.69 (br s, 3H), 1.70-1.79 (m, 1H), 1.93-2.16 (m, 5H), 2.21-2.33 (m, 1H), 2.36-2.47 (m, 4H), 4.72 (br s, 0.55H), 4.75 (br s, 0.55H), 5.04-5.14 (m, 1.5H) ppm.

$^{13}$C NMR (mixture of double bond isomers, 75 MHz, CHLOROFORM-d) δ 7.80, 7.84, 15.9, 17.65, 17.68, 21.7, 22.6, 25.7, 26.4, 26.6, 35.5, 35.8, 35.92, 35.97, 39.6, 41.7, 42.4, 109.5, 122.7, 124.0, 124.2, 131.4, 131.6, 136.2, 148.8, 211.5, 211.6 ppm.

Example 3: Compound of Formula (VII): Synthesis of (±)-2-ethyl-10-methyl-6-methyleneundec-9-enal and (E)-2-ethyl-6,10-dimethylundeca-5,9-dienal Reaction Step: f)

A 350 mL four-necked flask, equipped with magnetic stirrer, condenser, addition funnel, thermometer, argon adapter, syringe pump and oil bath, was inertized with argon and subsequently charged with (methoxymethyl)triphenylphosphonium chloride (45.2 mmol, 99.7% (2.0 equivalents) and suspended in dry THF (100 mL). The suspension was then cooled to −15° C. n-butyl lithium (29.4 mL of a 1.54 M solution in hexanes, 45.2 mmol, 2.0 equivalents) was added slowly over 35 min, during which the solution turned orange. The mixture was allowed to warm to 0° C. and stirred for 1 h. A solution of a mixture of 11-methyl-7-methylenedodec-10-en-3-one and (E)-7,11-dimethyldodeca-6,10-dien-3-one (example 2) (5.0 g, 22.6 mmol, 94.2% purity by qNMR, 1.0 equivalent) in THF (20 mL) was added dropwise over 45 min, while keeping the temperature at 0-5° C. The reaction was stirred for additional 30 min at 0° C. The reaction was allowed to warm to room temperature and stirred for 18 h. Subsequently, the reaction was cooled to 0° C. and quenched with brine (100 mL), resulting in two liquid phases and a colorless precipitate. Addition of water (50 mL) dissolved the precipitate; the aqueous phase was extracted with ethyl acetate (3×100 mL). The combined organic phases were washed with brine (2×50 mL), dried over MgSO$_4$, filtered and concentrated in vacuo, furnishing a dark red oil, from which a solid precipitated overnight at 4° C. The mixture was taken up in heptane/ethyl acetate 95:5 and then filtered through a plug of silica gel. The plug was flushed with additional heptane/ethyl acetate 95:5 and the combined filtrates were concentrated in vacuo, providing crude enol ether (7.85 g, 18.5 mmol, 55.7% purity by qNMR, 82% yield).

A 100 mL four-necked flask, equipped with thermometer, magnetic stirrer, argon adapter, condenser and oil bath, was charged with above crude enol ether (2.25 g, 5.30 mmol, 55.7%, 1.0 equivalent) and dissolved in acetone (48 mL) and water (12 mL). p-Toluenesulfonic acid monohydrate (102 mg, 0.53 mmol, 10 mol %, 98.5%) was added and the resulting yellow solution was heated to 62° C. (reflux) for 10 h. The reaction was allowed to cool to room temperature and diluted with ethyl acetate (30 mL). The aqueous phase was extracted with ethyl acetate (2×30 mL). The combined organic phases were washed with brine (2×20 mL), dried over MgSO$_4$, filtered and concentrated in vacuo, furnishing crude product as a yellow liquid (2.20 g, 3.66 mmol, 37.0% purity by qNMR, 69% yield) and purified by chromatography.

Characterization of Compound of Formula (VII)

GC-MS: 92.3 area %;

m/z (%) 222 (2, M$^+$), 204 [3, (M-H$_2$O)$^+$], 179 (8), 161 (16), 150 (3), 135 (9), 109 (27), 95 (13), 81 (14), 69 (100), 55 (11), 41 (45), 29 (7).

$^1$H NMR (300 MHz, CHLOROFORM-d) δ 0.92 (t, J=7.4 Hz, 3H), 1.40-1.75 (m, 12H), 1.97-2.24 (m, 7H), 4.72 (br s, 1H), 4.74 (br s, 1H), 5.06-5.16 (m, 1H), 9.59 (d, J=3.1 Hz, 1H) ppm.

$^{13}$C NMR (75 MHz, CHLOROFORM-d) δ 11.5, 17.7, 21.9, 25.1, 25.7, 26.4, 28.1, 35.9, 36.1, 53.3, 109.2, 124.1, 131.6, 149.0, 205.5 ppm.

Example 4: Compound of Formula (VI): Synthesis of (±)-(E)-5-ethyl-13-methyl-9-methylenetetradeca-3,12-dien-2-one Reaction Step: e)

A 100 mL four-necked flask, equipped with magnetic stirrer, condenser, thermometer, argon adapter and oil bath, was inertized with argon and subsequently charged with a mixture of 2-ethyl-10-methyl-6-methyleneundec-9-enal and (E)-2-ethyl-6,10-dimethylundeca-5,9-dienal (example 3) (6.50 g, 24.7 mmol, 84.6% purity by qNMR, ratio ~95:5, 1.0 equivalent) and 1-(triphenylphosphoranylidene)-2-propanone (11.9 g, 37.1 mmol, 99%, 1.5 equivalents), and dissolved in toluene (60 mL). The colorless suspension was heated to 125° C. (oil bath) for 26 h. The reaction mixture was allowed to cool to room temperature and the solvent was removed in vacuo. The residue was suspended in heptane (50 mL) and stirred for 30 min at 23° C. The suspension was filtered and the filtrate was concentrated in vacuo, furnishing a yellow liquid (7.85 g). The crude product was purified by flash chromatography on silica gel (220 g), eluting with heptane/tert-butyl methyl ether 100:0 to 90:10 (v/v), flow rate 150 mL/min. Some mixed fractions were purified again by flash chromatography, and the combined product fractions furnished (±)-(E)-5-ethyl-13-methyl-9-methylenetetradeca-3,12-dien-2-one (4.88 g, 17.5 mmol, 94.3% purity by qNMR, 71% yield).

Characterization of Compound of Formula (VI)

GC-MS: 96.3 area % ((E)-5-ethyl-13-methyl-9-methylenetetradeca-3,12-dien-2-one)

m/z (%) 262 (3, M$^+$), 244 [1, (M-H$_2$O)$^+$], 233 [1, (M-C$_2$H$_5$)$^+$], 219 (3), 201 (3), 189 (3), 178 (5), 161 (13), 149 (7), 135 (21), 122 (17), 109 (49), 95 (36), 81 (23), 69 (100), 55 (19), 41 (59), 29 (4).

$^1$H NMR (300 MHz, CHLOROFORM-d) δ 0.86 (m, J=7.3 Hz, 3H), 1.25-1.59 (m, 6H), 1.61 (s, 3H), 1.69 (d, J=0.9 Hz, 3H), 1.93-2.16 (m, 7H), 2.25 (s, 3H), 4.70 (br s, 1H), 4.72 (br s, 1H), 5.05-5.16 (m, 1H), 6.04 (dd, J=15.9, 0.7 Hz, 1H), 6.56 (dd, J=15.9, 9.1 Hz, 1H) ppm.

$^{13}$C NMR (75 MHz, CHLOROFORM-d) δ 11.64 (s, 1C), 17.7 (1C), 25.3 (1C), 25.7 (1C), 26.4 (1C), 26.9 (1C), 27.2 (1C), 33.7 (1C), 35.9 (1C), 36.1 (1C), 44.5 (1C), 109.0 (1C), 124.1 (1C), 131.2 (1C), 131.5 (1C), 149.2 (1C), 152.4 (1C), 198.6 (1C) ppm.

Example 5: Compound of Formula (IV): Synthesis of (all-rac)-5-ethyl-9,13-dimethyltetradecan-2-one Reaction Step: d)

(E)-5-ethyl-13-methyl-9-methylenetetradeca-3,12-dien-2-one (example 4) (3.18 g, 11.3 mmol, 93.5%) was dissolved in heptane (10 g) and treated with charcoal (1.00 g). After 5 min stirring, the suspension was filtered and the filter cake was washed with heptane (10 g). The filtrate was transferred into a 125 mL autoclave, diluted with heptane (10 g) and Pd/C (150 mg, 5% Pd, 0.071 mmol, 0.6 mol %) was added. The reactor was inertized with argon, stirred at 500 rpm, heated to 80° C. and finally pressurized with hydrogen to 2 bara for 2 h. The reaction was allowed to cool to room temperature, the suspension was filtered via syringe filter (0.45 μm) and the cake was washed with heptane (21.7 g). The filtrate was concentrated in vacuo, furnishing (all-rac)-5-ethyl-9,13-dimethyltetradecan-2-one as colorless oil (3.00 g, 96.4% by qNMR, 10.8 mmol, 95% yield).

Characterization of Compound of Formula (IV)

GC-MS: 98.4 area %;

m/z (%) 268 (1, M$^+$), 253 [2, (M-CH$_3$)$^+$], 239 [1, (M-C$_2$H$_5$)$^+$], 210 (14), 155 (4), 141 (5), 124 (15), 113 (10), 95 (11), 85 (20), 71 (100), 57 (36), 43 (80), 29 (7).

$^1$H NMR (300 MHz, CHLOROFORM-d) δ 0.81-0.90 (m, 12H), 0.99-1.44 (m, 16H), 1.45-1.60 (m, 3H), 2.15 (s, 3H), 2.34-2.46 (m, 2H) ppm.

$^{13}$C NMR (75 MHz, CHLOROFORM-d) δ 10.73, 10.77, 19.69, 19.71, 22.61, 22.71, 24.0, 24.8, 25.61, 25.68, 27.06, 27.11, 28.0, 29.8, 32.8, 33.3, 37.3, 37.5, 38.5, 39.4, 41.26, 41.29, 209.6 ppm.

Example 6: Compound of Formula (II-A): Synthesis of (all-rac)-6-ethyl-3,10,14-trimethylpentadec-1-en-3-ol Reaction Step: c3)

An oven-dried 25 mL three-necked round-bottom flask was charged with vinylmag-nesium chloride (2.1 mL of a 1.6 M solution in THF, 3.35 mmol, 1.5 equivalents). A solution of 5-ethyl-9,13-dimethyltetradecan-2-one (example 5) (0.65 g, 2.24 mmol, 92.3% by qNMR) in dry THF (2.2 mL) was added dropwise at 23° C. over 30 min. The reaction was stirred for an additional 2 h at 23° C., after which it was quenched with sat. aq. NH$_4$Cl solution (1 mL). Heptane (10 mL) and brine (10 mL) were added. The aqueous phase was extracted with heptane (2×10 mL). The combined organic phases were washed with brine (2×10 mL), dried over MgSO$_4$, filtered and concentrated in vacuo, furnishing (all-rac)-6-ethyl-3,10,14-trimethylpentadec-1-en-3-ol as colorless oil (0.70 g, 2.0 mmol, 84.7% purity by qNMR, 89% yield).

Characterization of Compound of Formula (II-A)

GC-MS: 97.4 area %;

m/z (%) 296 (0.1, M$^+$), 278 [1, (M-H$_2$O)$^+$], 236 (2), 207 (2), 193 (2), 151 (3), 137 (3), 123 (9), 109 (5), 95 (5), 81 (6), 71 (100), 57 (13), 43 (23), 29 (2).

$^1$H NMR (300 MHz, CHLOROFORM-d) δ 0.79-0.90 (m, 12H), 1.06-1.44 (m, 22H), 1.46-1.65 (m, 3H), 5.05 (dd, J=10.7, 1.3 Hz, 1H), 5.21 (dd, J=17.3, 1.3 Hz, 1H), 5.92 (dd, J=17.3, 10.7 Hz, 1H) ppm.

$^{13}$C NMR (75 MHz, CHLOROFORM-d) δ 10.82, 10.85, 10.88, 14.1, 19.7, 22.61, 22.69, 22.71, 24.10, 24.12, 24.8, 25.78, 25.84, 26.87, 26.93, 27.64, 27.67, 28.0, 29.0, 31.9, 32.7, 33.4, 37.3, 37.5, 39.1, 39.28, 39.30, 39.37, 73.4, 111.5, 145.3 ppm.

Example 7: Compound of Formula (I-A): Synthesis of (all-rac)-2-(3-ethyl-7,11-dimethyldodecyl)-2,5,7,8-tetramethylchroman-6-ol Reaction Step: b2)

A 5 mL round-bottom flask equipped with magnetic stirrer, septum and argon-balloon was charged with 2,3,5-trimethylhydroquinone (0.21 g, 1.34 mmol, 98%, 1.0 equivalent), ZnCl$_2$ (0.16 g, 1.13 mmol, 98%, 0.84 equivalent) and suspended in ethyl acetate (1 mL) and conc. HCl (22 mg, 0.22 mmol, 0.17 equivalent). The reaction was heated to 35° C. (oil bath). 6-ethyl-3,10,14-trimethylpentadec-1-en-3-ol (example 6) (0.47 g, 1.34 mmol, 84.7% by qNMR, 1.0 equivalent) was then added via syringe within 30 min. Subsequently, the reaction was stirred for 2 h at 35° C. The mixture was then diluted with heptane (5 mL) and water (2.5 mL). The aqueous phase was extracted with heptane (5 mL). The combined organic phases were washed with water (2×2.5 mL), 10% aq. NaHCO$_3$ solution (2.5 mL) and brine (2.5 mL). The organic phases were dried over MgSO$_4$, filtered and concentrated in vacuo, furnishing (all-rac)-2-(3-ethyl-7,11-dimethyldodecyl)-2,5,7,8-tetramethylchroman-6-ol as a brown oil (0.51 g, 1.05 mmol, 88.8% by qNMR, 78% yield).

Characterization of Compound of Formula (I-A)

GC-MS: 99.5 area %;

m/z (%) 430 (89, M$^+$), 205 (13), 165 (100), 121 (6), 91 (2), 71 (3), 57 (6), 43 (14).

$^1$H NMR (300 MHz, CHLOROFORM-d) δ 0.84 (t, J=7.4 Hz, 3H), superimposed by 0.85 (d, J=6.4 Hz, 3H), 0.88 (d, J=6.8 Hz, 6H), 1.03-1.42 (m, 18H), superimposed by 1.23 (s, 3H), 1.44-1.63 (m, 3H), 1.69-1.93 (m, 2H), 2.12 (s, 6H), 2.17 (s, 3H), 2.61 (t, J=6.9 Hz, 2H), 4.17 (s, 1H, OH) ppm.

$^{13}$C NMR (75 MHz, CHLOROFORM-d) δ 10.81, 10.86, 10.89, 10.93, 11.3, 11.8, 12.2, 19.7, 20.8, 22.6, 22.7, 23.7, 24.07, 24.16, 24.8, 25.78, 25.85, 25.90, 25.97, 26.45, 26.51, 28.0, 31.37, 31.39, 32.78, 33.43, 33.54, 36.50, 36.53, 36.57, 37.4, 37.5, 39.2, 39.4, 74.6, 117.3, 118.4, 121.0, 122.6, 144.5, 145.6 ppm.

Example 8: Example of Compound of Formula (I-B): Synthesis of (all-rac)-2-(3-ethyl-7,11-dimethyldodecyl)-2,5,7,8-tetramethylchroman-6-yl acetate Reaction Step: A2)

A 5 mL round-bottom flask equipped with magnetic stirrer, condenser and argon adapter was charged with 2-(3-ethyl-7,11-dimethyldodecyl)-2,5,7,8-tetramethyl-chroman-6-ol (example 7) (0.41 g, 0.85 mmol, 88.8% by qNMR, 1.0 equivalent) and dissolved in acetic anhydride (0.23 mL, 0.24 g, 99%, 2.8 equivalents) and pyridine (13.7 uL, 13.4 mg, 0.17 mmol, 99.8%, 0.2 equivalents) and heated to 90° C. (oil bath) for 1.5 h. The reaction was allowed to cool to room temperature and then concentrated in vacuo, furnishing crude product (476 mg).

Purification by flash chromatography (silica gel, heptane/ethyl acetate gradient 100:0 to 90:10 v/v) furnished (all-rac)-2-(3-ethyl-7,11-dimethyldodecyl)-2,5,7,8-tetramethyl-chroman-6-yl acetate as pale yellow oil (392 mg, 0.79 mmol, 94.9% by qNMR, 93% yield).

Characterization of Compound of Formula (I-B)

GC-MS: 99.7 area %;

m/z (%) 472 (11 M$^+$), 430 [100, (M-Ac)$^+$], 247 (4), 207 (20), 165 (56), 121 (3), 91 (2), 71 (3), 57 (7), 43 (16).

$^1$H NMR (300 MHz, CHLOROFORM-d) δ 0.85 (t, J=7.2 Hz, 3H), superimposed by 0.86 (d, J=6.40 Hz, 3H), 0.88 (d, J=6.6 Hz, 6H), 1.06-1.42 (m, 18H), superimposed by 1.24 (s, 3H), 1.45-1.64 (m, 3H), 1.68-1.90 (m, 2H), 1.99 (s, 3H), 2.04 (s, 3H), 2.11 (s, 3H), 2.34 (s, 3H), 2.60 (t, J=6.8 Hz, 2H) ppm.

$^{13}$C NMR (75 MHz, CHLOROFORM-d) δ 10.82, 10.84, 10.86, 10.91, 11.8, 12.1, 12.9, 19.7, 20.55, 20.60, 22.62, 22.71, 24.09, 24.15, 24.8, 25.76, 25.84, 25.87, 25.94, 26.41, 26.48, 28.0, 32.8, 33.42, 33.51, 37.3, 37.5, 39.1, 39.4, 75.2, 117.3, 123.0, 124.9, 126.6, 140.5, 149.4, 169.7 ppm.

Olfactory Properties

The odor of the individual substances has been tested by different test persons by sniffing at the smelling strip on which the respective substance has been deposed by means of a pipette. The olfactory impression has been summarized in table 1

TABLE 1

| Olfactory impressions of the compounds | | | |
|---|---|---|---|
| Example | Compound | Head note | Heart note |
| Example 1 | Formula (IX) | — | cellar, fusty |
| Example 2 | Formula (VIII) | fruity, pear | fruity, pear |
| Example 3 | Formula (VII) | damp wood | fruity, pear |
| Example 4 | Formula (VI) | aromatic | — |
| Example 5 | Formula (IV) | chocolate, bean | — |

Antioxidant Properties a) Determination of the Oxidative Stability by Determination of the Induction Period Oxidative stability was assessed using a Rancimat™ (Metrohm AG, Zofingen, Switzerland). The Rancimat™ is designed to monitor the oxidation of liquid products. In principle, purified heated air is passed through the samples and volatile oxidation products are transferred into a flask of demineralized water. The conductivity of the water is monitored by an electrode and volatile oxidation products such as acetic acid or other charged molecules will cause a rise of conductivity of the water over time. These oxidation processes start slowly but exponentially accelerate after an induction time which is indicative for the oxidative stability of the compound or sample (DGF Standard Method C-VI 6f (06)). So, the longer the induction time measured is, the higher the antioxidant activity is.

Approximately 1 g of 2-(3-ethyl-7,11-dimethyldodecyl)-2,5,7,8-tetramethyl-chroman-6-ol (example 7) or alpha-tocopherol (Ref. 1) were loaded into the Rancimat™ flask and placed inside the device. Purified air at a temperature of 80° C. was purged through the sample into a plastic flask containing demineralized water (MilliQ water) and the conductivity of the water was measure continuously. The data was visualized by plotting the time on the x-axis and the conductivity on the y-axis. The slope of the resulting graph increased slowly until the induction time was reached. An exponentially increase of oxidation reactions is indicated by a rapid increase of the slope of the curve. The induction time is determined manually as intersection of the tangents and compiled in table 2.

TABLE 2

| Oxidative stability by means of Rancimat ™ test at 80° C. | |
|---|---|
| Example | Induction time [hours] |
| Example 7 | 42 |
| Ref. 1 | 31 |

Table 2 shows an induction time which is 35% longer than the induction time of alpha-tocopherol which is well-known for its antioxidant activities.

b) Determination of the Antioxidant Activity by Reaction with 2,2'-Diphenyl-1-Picrylhydrazyl (DPPH)

The determination of the antioxidant activity was further assessed with a validated colorimetric method (Planck, Szpylka, Sapirstein, Woolard, Zapf, Lee, Chen, Liu, Tsao, Düsterloh, Baugh, Determination of the antioxidant activity by reaction with 2,2'-Diphenyl-1-Picrylhydrazyl (DPPH): Collaborative Study first Action 2012.04, J AOAC, 95, 2012: 1562-9).

In principle, the antioxidant is dissolved in water:methanol and an aliquot of the solution reacts with the pink coloured stabile radical DPPH. This reaction leads to the formation of colourless antioxidant-DPPH adducts and the decrease in colour can be quantified spectrophotometrically at 517 nm. The assay is calibrated with the water-soluble antioxidant Trolox.

Approximately 25 mg of 2-(3-ethyl-7,11-dimethyldodecyl)-2,5,7,8-tetra-methylchroman-6-ol (example 7) or alpha-tocopherol (Ref. 1) were dissolved in 50 mL of methanol/water (40:10, v/v). 0.4 mL of these solutions were added to the DPPH reagent solution (approx. 40 mg/L), mixed and kept in the dark for 30 min. The solutions were measured spectrophotometrically against a distilled water blank at 517 nm. In parallel, a calibration curve with Trolox (=6-hydroxy-2,5,7,8-tetramethylchroman-2-carboxylic acid) was prepared at 100, 200, 300, and 400 μg/mL according to the method cited above.

The antioxidant activity for both compounds were calculated as Trolox equivalents and are reported in table 3.

TABLE 3

DPPH assay performance compared to Trolox.

| Example | Trolox equivalents |
|---------|-------------------|
| Example 7 | 1.17 |
| Ref. 1 | 1.15 |

Table 3 shows that example 7 as well as the Ref. 1 have a higher antioxidant activity than Trolox which is a well-established antioxidant.

Table 3, furthermore, shows that example 7 shows a higher antioxidant activity than alpha-tocopherol (Ref. 1).

c) Redox Potential

Cyclic voltammetry experiments were performed with a PGSTAT128N (Metrohm Autolab). The electrochemical cell consisted in a three-electrode system: a glassy carbon working electrode (BASi MF-2012), a platinum wire counter electrode and a Ag/Ag+reference electrode filled with 0.1 M LiClO$_4$ ethanol-acetonitrile (1:1) solution. The working electrode was cleaned with a polishing cloth (Buehler) impregnated with a 0.05 mm alumina slurry and sonicated. Between runs, the electrode was rinsed with the solvent and dried with a powder-free tissue.

A 10 mM stock solution of 2-(3-ethyl-7,11-dimethyldodecyl)-2,5,7,8-tetra-methylchroman-6-ol (example 7) was prepared by dissolving example 7 into a 0.1 M LiClO$_4$ ethanol-acetonitrile (1:1) buffer previously prepared.

The above mentioned stock solutions were then spiked into 0.1 M LiClO$_4$ ethanol-acetonitrile (1:1) buffer solution in order to obtain the desired analyte concentrations. The cyclic voltammetry experiments were performed by scanning the potential (scan rate: 0.05 V/s, potential step: 0.001 V), first obtaining the anodic wave (from 0 V to 0.7 V) and then cycling the potential back from 0.7 V to 0 V for obtaining the cathodic wave.

Figure 3:
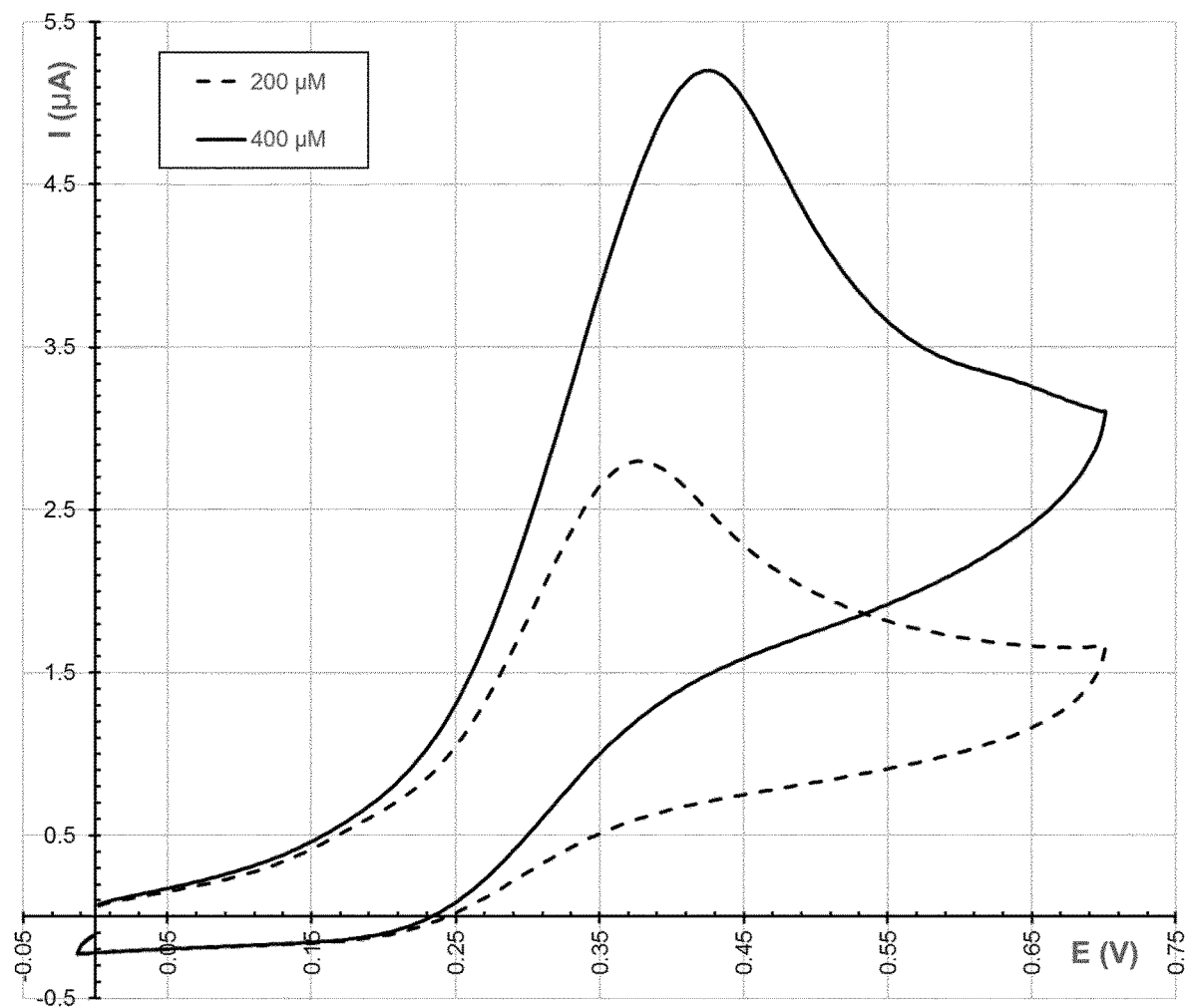

FIG. 3 shows in the x-axis the applied potential (E) in Volt and the measured electric current (I) in micro ampere for the example 7 at a concentration of 200 μM (dashed line), or of 400 μM (solid line), respectively.

The redox potential of example 7 was taken from the voltammetries' cathodic waves as maximum peak in FIG. 3 and are reported in table 4.

TABLE 4

Redox potential of example 7.

| concentration | Redox potential |
|---------------|-----------------|
| 200 μM | 0.38 V |
| 400 μM | 0.43 V |

The redox potential values measured electrochemical clearly indicate an excellent antioxidant behavior of 2-(3-ethyl-7,11-dimethyldodecyl)-2,5,7,8-tetra-methylchroman-6-ol (example 7).

The invention claimed is:

1. A compound of formula (I):

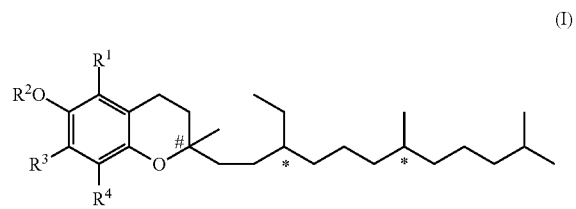

(I)

wherein $R^1$, $R^3$ and $R^4$ represent independently from each other hydrogen or methyl groups;

$R^2$ represents hydrogen or $R^{2'}$ which is a phenol protecting group; and wherein each * marks a chiral/stereogenic centre, and # marks a chiral/stereogenic centre.

2. The compound according to claim 1, wherein $R^{2'}$ is selected from the groups consisting of:

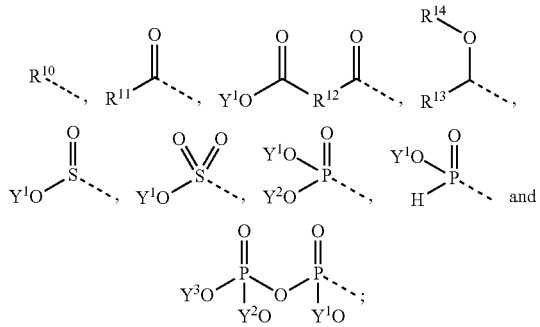

wherein $R^{10}$ and $R^{11}$ represent independently from each other a $C_{1-15}$-alkyl or a fluorinated $C_{1-15}$-alkyl or a $C_{1-15}$-cycloalkyl or a $C_{7-15}$-aralkyl group;

$R^{12}$ represents a $C_{1-15}$-alkylene or a $C_{6-15}$-alkylene group;

and wherein either $R^{13}$ represents a $C_{1-15}$-alkyl group or an alkyleneoxyalkyl group or a polyoxyalkylene group;

$R^{14}$ represents hydrogen or a $C_{1-15}$-alkyl group;

or $R^{13}$ and $R^{14}$ represent together a $C_{3-7}$-alkylene group forming a 5 to 7 membered ring; and wherein $Y^1$, $Y^2$ and $Y^3$ represent independently from each other hydrogen or a group of the formula:

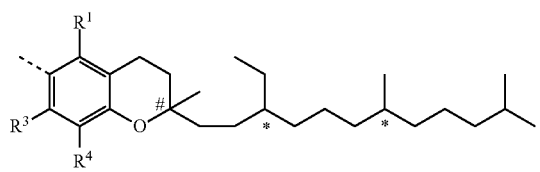

and wherein the single dotted line represents the bond by which said substituent is bound to the rest of a molecule.

3. The compound according to claim 1, wherein the compound of formula (I) is of formula (I-A):

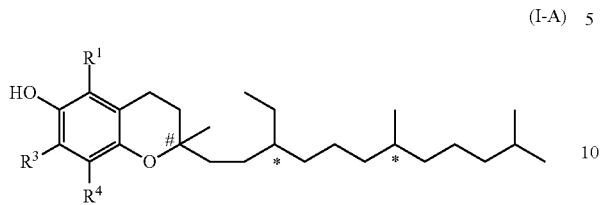
(I-A)

wherein each * marks a chiral/stereogenic centre, and # marks a chiral/stereogenic centre.

4. A compound of formula (IV):

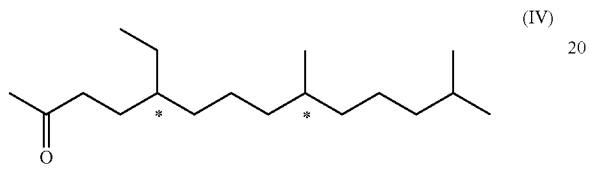
(IV)

wherein each * marks a chiral/stereogenic centre.

5. A process of manufacturing a compound of formula (IV):

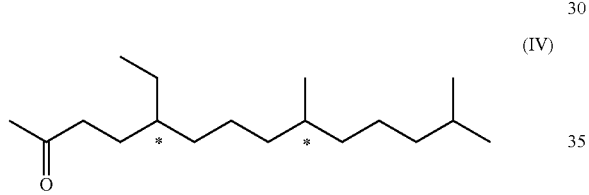
(IV)

comprising the step of:
d) hydrogenating a compound of formula (VI):

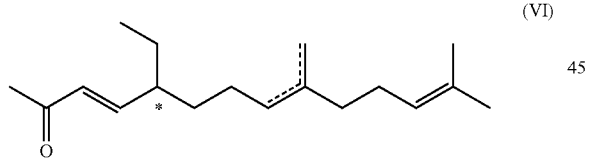
(VI)

to yield the compound of formula (IV), wherein the dotted line indicates a carbon-carbon double bond which is located at one of the two indicated positions.

6. A compound of formula (VI):

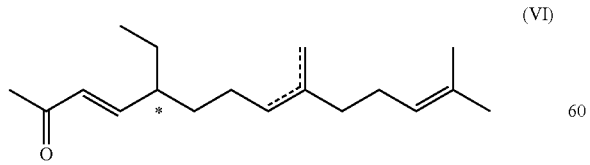
(VI)

wherein the dotted line indicates a carbon-carbon double bond which is located at one of the two indicated positions; and wherein
each * marks a chiral/stereogenic centre.

7. A compound of formula (VII):

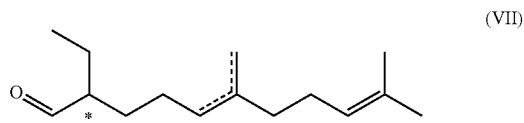
(VII)

wherein the dotted line indicates a carbon-carbon double bond which is located at one of the two indicated positions; and wherein
each * marks a chiral/stereogenic centre.

8. A process of manufacturing the compound of formula (II-A):

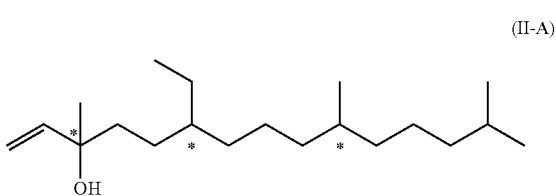 [SMILES: C=CC(C)(O)CCC(CC)CCCC(C)CCCC(C)C]
(II-A)

comprising the step
b) providing a compound of formula (IV):

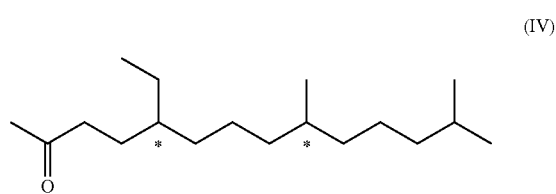 [SMILES: CCC(CCCC(C)CCCC(C)C)CCC(C)=O]
(IV)

followed by the steps of either:
c1) ethinylating the compound of formula (IV) using ethyne in the presence of a basic substance to yield a compound of formula (V):

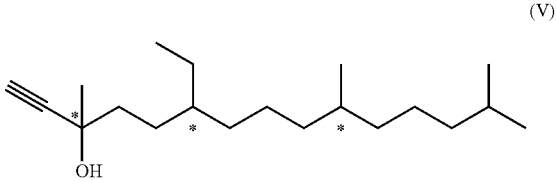 [SMILES: C#CC(C)(O)CCC(CC)CCCC(C)CCCC(C)C]
(V)

c2) hydrogenating the compound of formula (V) with molecular hydrogen in the presence of a Lindlar catalyst to yield the compound of formula (II-A); or c3) vinylating the compound of formula (IV) by addition of a vinyl Grignard reagent to yield the compound of formula (II-A); wherein each * marks a chiral/stereogenic centre.

9. The process according to claim 8, which produces the compound of formula (VII):

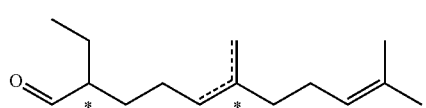
(VII)

wherein the dotted line indicates a carbon-carbon double bond which is located at one of the two indicated positions; and wherein
each * marks a chiral/stereogenic centre.

10. A compound of formula (V):

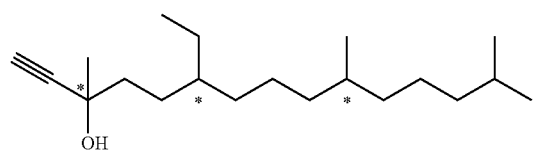
(V)

wherein each * marks a chiral/stereogenic centre.

11. A compound of formula (II-A):

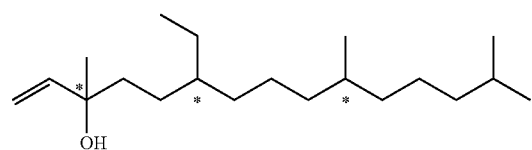
(II-A)

wherein each * marks a chiral/stereogenic centre.

12. A process of manufacturing the compound of formula (II-B):

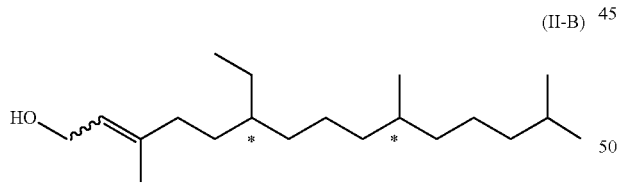
(II-B)

wherein the process comprising conducting isomerization of a compound of formula (II-A):

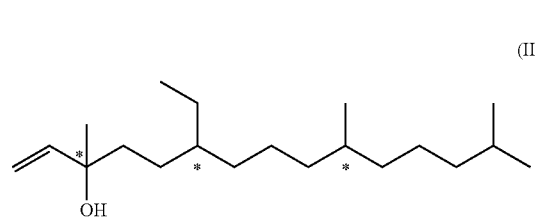
(II-A)

wherein each * marks a chiral/stereogenic centre; and wherein
the wavy line represents a carbon-carbon bond which when linked to the carbon-carbon double bond is either in the Z- or in the E-configuration.

13. A compound of formula (II-B):

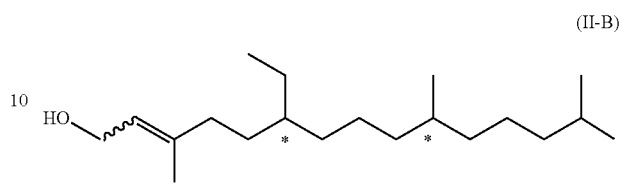
(II-B)

wherein each * marks a chiral/stereogenic centre; and wherein
the wavy line represents a carbon-carbon bond which when linked to the carbon-carbon double bond is either in the Z- or in the E-configuration.

14. A process of manufacturing a compound of formula (I-A) comprising the steps of:
b1) providing a compound of formula (II-A) or (II-B):

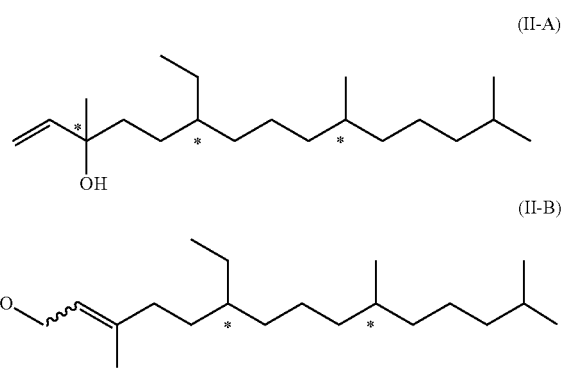
(II-A)

(II-B)

b2) condensing the compound of formula (II-A) or (II-B) with a compound of formula (III) to yield the compound of formula (IA)

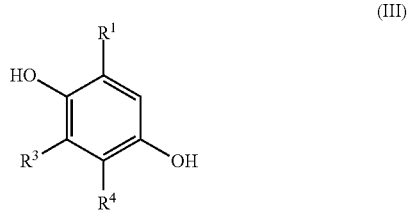
(III)

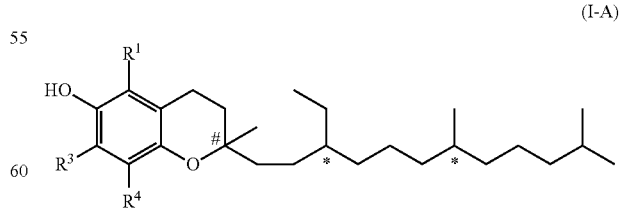
(I-A)

wherein $R^1$, $R^3$ and $R^4$ represent independently from each other hydrogen or methyl groups; and wherein
each * marks a chiral/stereogenic centre, and # marks a chiral/stereogenic centre; and wherein the wavy line represents a carbon-carbon bond which when linked to the carbon-carbon double bond is either in the Z- or in the E-configuration.

15. A process of manufacturing a compound of formula (I-B) comprising the steps of:
a1) providing a compound of formula (I-A):

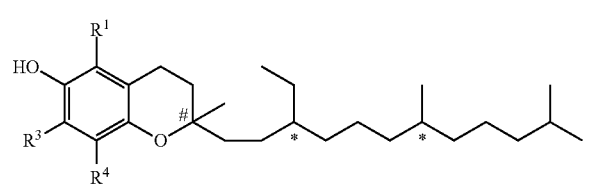

(I-A)

a2) reacting the compound of formula (I-A) with a protecting agent to yield the compound of formula (I-B):

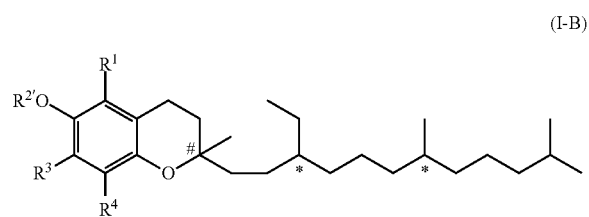

(I-B)

wherein $R^1$, $R^3$ and $R^4$ represent independently from each other hydrogen or methyl groups; and
$R^{2'}$ represents a phenol protecting group; and wherein each * marks a chiral/stereogenic centre, and # marks a chiral/stereogenic centre.

16. A composition comprising a compound of formula (I) and a compound of formula (XI):

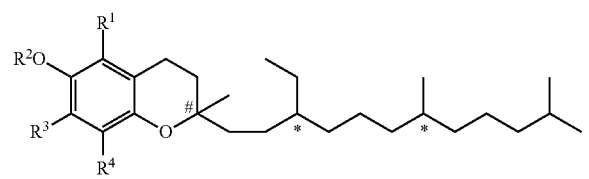

(I)

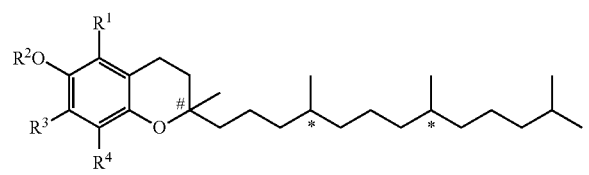

(XI)

wherein $R^1$, $R^3$ and $R^4$ represent independently from each other hydrogen or methyl groups;
$R^2$ represents hydrogen or $R^{2'}$ which is a phenol protecting group; and wherein
each * marks a chiral/stereogenic centre, and # marks a chiral/stereogenic centre.

17. An antioxidant which comprises the compound of formula (I) according to claim 1.

18. A flavour or fragrance composition which comprises the compound of formula (IV), (VI), (VII), (V), (II-A) or (II-B):

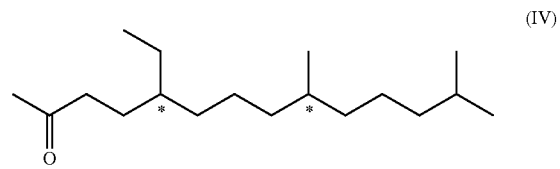

(IV)

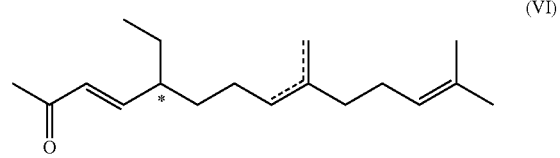

(VI)

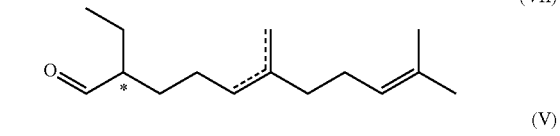

(VII)

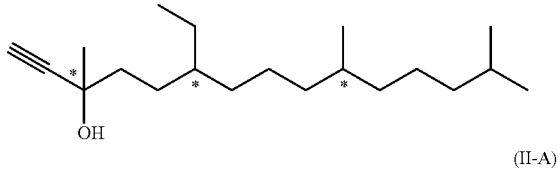

(V)

(II-A)

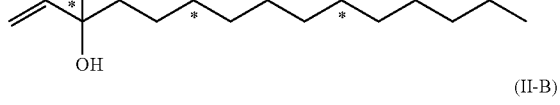

(II-B)

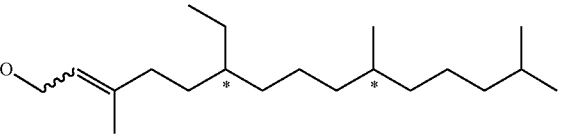

wherein the dotted line indicates a carbon-carbon double bond which is located at one of the two indicated positions; and wherein
each * marks a chiral/stereogenic centre.

* * * * *